United States Patent [19]

Schwager

[11] Patent Number: 5,728,042
[45] Date of Patent: Mar. 17, 1998

[54] MEDICAL APPLIANCE FOR IONIZING RADIATION TREATMENT HAVING RADIOPAQUE MARKERS

[75] Inventor: Michael Schwager, Winterthur, Switzerland

[73] Assignee: Schneider (Europe) A.G., Bulach, Switzerland

[21] Appl. No.: 581,098

[22] Filed: Dec. 29, 1995

[30] Foreign Application Priority Data

Jun. 22, 1995 [EP] European Pat. Off. .............. 95109741

[51] Int. Cl.$^6$ .............................. A61N 5/00; A61N 5/10
[52] U.S. Cl. ........................................ 600/3; 600/1; 600/7
[58] Field of Search .............................. 600/1, 3, 7

[56] References Cited

U.S. PATENT DOCUMENTS

| | | | |
|---|---|---|---|
| 1,442,051 | 1/1923 | Cummings . | |
| 3,324,847 | 6/1967 | Zoumboulis | 128/1.2 |
| 3,674,006 | 7/1972 | Holmer | 600/7 |
| 3,811,426 | 5/1974 | Culver et al. | 128/1.2 |
| 3,927,325 | 12/1975 | Hungate et al. | 250/435 |
| 3,970,073 | 7/1976 | Greene | 128/1.2 |
| 4,402,308 | 9/1983 | Scott | 128/1.2 |
| 4,588,395 | 5/1986 | Lemelson | 604/59 |
| 4,610,662 | 9/1986 | Weikl et al. | 604/53 |
| 4,697,575 | 10/1987 | Horowitz | 128/1.2 |
| 4,770,653 | 9/1988 | Shturman | 604/21 |
| 4,940,452 | 7/1990 | Rohe et al. | 600/7 |
| 4,960,411 | 10/1990 | Buchbinder | 604/95 |
| 4,983,167 | 1/1991 | Sahota | 606/194 |
| 4,994,013 | 2/1991 | Suthanthiran et al. | 600/8 |
| 5,012,357 | 4/1991 | Schdeppez et al. | 600/7 |
| 5,059,166 | 10/1991 | Fischell et al. | 600/3 |
| 5,106,360 | 4/1992 | Ishiwara et al. | 600/2 |
| 5,120,973 | 6/1992 | Rohe et al. | 250/497 |
| 5,147,282 | 9/1992 | Kan | 600/1 |
| 5,199,393 | 4/1993 | Dake et al. | 600/3 |
| 5,213,561 | 5/1993 | Weinstein et al. | 600/3 |
| 5,282,781 | 2/1994 | Liprie | 600/3 |
| 5,302,168 | 4/1994 | Hess | 600/3 |
| 5,354,257 | 10/1994 | Roubin et al. | 600/3 |
| 5,395,300 | 3/1995 | Liprie | 600/3 |
| 5,405,309 | 4/1995 | Carden, Jr. | 600/3 |
| 5,411,466 | 5/1995 | Hess | 600/3 |
| 5,498,227 | 3/1996 | Mawad | 600/3 |
| 5,503,613 | 4/1996 | Weinberger | 600/3 |
| 5,503,614 | 4/1996 | Liprie | 600/7 |
| 5,520,194 | 5/1996 | Miyata et al. | 128/772 |
| 5,540,659 | 7/1996 | Teirstein | 604/104 |
| 5,643,171 | 7/1997 | Bradshaw et al. | 600/1 |

FOREIGN PATENT DOCUMENTS

| | | | |
|---|---|---|---|
| 0152124A3 | 8/1985 | European Pat. Off. | A61N 5/10 |
| 0158630A3 | 10/1985 | European Pat. Off. | A61N 5/00 |
| 0308630A1 | 3/1989 | European Pat. Off. | A61N 5/10 |
| 0433011A1 | 6/1991 | European Pat. Off. | A61F 2/06 |
| 0447745A2 | 9/1991 | European Pat. Off. | A61M 36/12 |
| 0466681A1 | 1/1992 | European Pat. Off. | A61N 5/10 |

(List continued on next page.)

OTHER PUBLICATIONS

Pending U.S. Patent application Serial No. 08/276,219, filed Jun. 28, 1994, claiming priority to EP 93110531.6 which is commonly owned by the assignee of the above–captioned application.

Pending U.S. application Serial No. 08/489,464, filed Jun. 12, 1995, claiming priority to EP 94108913.8, which is commonly owned by the assignee of the above–captioned application.

(List continued on next page.)

*Primary Examiner*—William E. Kamm
*Assistant Examiner*—Carl H. Layno
*Attorney, Agent, or Firm*—Peter C. Richardson; Lawrence C. Akers; Philip C. Strassburger

[57] ABSTRACT

The appliance comprises a core wire on which is mounted a coil of radioactive material. A first proximal radiopaque coil configuration and a second distal radiopaque coil configuration maintain and locate the radioactive radiation coil on the core wire thereby assuring positioning thereof on the core wire and accurate visualization via X-ray fluoroscopy.

27 Claims, 2 Drawing Sheets

FOREIGN PATENT DOCUMENTS

| | | | |
|---|---|---|---|
| 0474994A1 | 3/1992 | European Pat. Off. | A61N 5/10 |
| 0621015A1 | 10/1994 | European Pat. Off. | |
| 0633041A1 | 1/1995 | European Pat. Off. | |
| 0668088A1 | 8/1995 | European Pat. Off. | |
| 0686342A1 | 12/1995 | European Pat. Off. | A01N 1/00 |
| 1065989 | 9/1959 | Germany. | |
| 3620123A1 | 12/1987 | Germany. | |
| 9102312 | 8/1992 | Germany | A61M 36/04 |
| 793158 | 4/1958 | United Kingdom | A61N 5/10 |
| 8604248 | 7/1986 | WIPO | 600/7 |
| 9200776 | 1/1992 | WIPO | A61M 36/12 |
| 92/03179 | 3/1992 | WIPO. | |
| 93/04735 | 3/1993 | WIPO. | |
| 94/16646 | 8/1994 | WIPO. | |
| 95/30384 | 11/1995 | WIPO. | |
| 9606654 | 3/1996 | WIPO | A61M 29/00 |
| 96/13303 | 5/1996 | WIPO. | |
| 96/17654 | 6/1996 | WIPO. | |

OTHER PUBLICATIONS

"Strontium—90—Applikator für interstitielle Bestrahlung der Hypophyse," Fortschritte auf dem Begiete der Röntgenstrahlen und den Nuklearmedizin, Holmer et al., pp. 524–578 (1867), with English translation.

"Suppresion of Intimal Proliferation after Balloon Angioplasty with Local Beta Irradiation in Rabbits," Shefer et al., JACC vol. 21 No. 2, 889–25 (Feb. 1993).

"Prophylaxis of Intimal Hyperplasia after Stent–Implantation in Peripheral Arteries Using Endovascular Irradiation," Böttcher et al., International Journal of Radiation Oncology Biology Physics, vol. 24, Supplement 1, p. 171, (1992).

Introduction to Modern Physics, Richtmyer, Kennard, and Lauritsen, Fifth Edition, 1995.

The Atomic Nucleus, Robley D. Evans, Ph.D., Massachusetts Institute of Technology, 1955.

Proliferation Studies of the Endothelial and Smooth Muscle Cells of the Mouse Mesentery After Irradiation, D. G. Hirst et al., Gray Laboratory of the Cancer Research Campaign, Mount Vernon Hospital, Norwood, Middlesex, Cell Tissue Kinet. (1980) 13, pp. 91–104.

51. The Potential of a beta–particle emitting stent to inhibit re–stenosis following catheter–based revascularisation: work in progress, R. E. Fischell, et al., unknown publication date.

Intra–arterial Beta Irradiation Prevents Neointimal Hyperplasia in a Hypercholesterolemic Rabbit Restenosis Model, Vitali Verin and Youri Popowski (co–inventors of the above–captioned application) et al., 1995 American Heart Association, Inc.

High Dose Rate Brachytherapy for Prevention of Restenosis After Percutaneous Transluminal Coronary Angioplasty: Preliminary Dosimetric Tests of a New Source Presentation, Youri Popwski and Vitali Verin (co–inventors of the above–captioned application) et al., accepted for publication Feb. 24, 1995, Int. J. Radiation Oncology Biol. Phys., vol. 33, No. 1, pp. 211–215, 1995.

Intra–Arterial $^{90}Y$ Brachytherapy: Preliminary Dosimetric Study Using a Specially Modified Angioplasty Balloon, Youri Popowski and Vitali Verin (co–inventors of the above–captioned application) et al., Int. J. Radiation Oncology Biol. Phys., vol. 33, No. 3, pp. 713–717, 1995.

Effects of High Dose Intracoronary Irradiation on Vasomotor Function and Smooth Muscle Histopathology, Joseph G. Wiedermann, M.D., et al., unknown publication date, listed in file history of U.S. patent No. 5,503,617 as published Oct. 1992.

Intracoronary Irradiation Markedly Reduces Restenosis After Balloon Antgioplasty in a Porcine Model, Joseph G. Wiedermann, M.D., et al., of unknown publication date, listed in file history of U.S. Patent No. 5,503,617, as published Oct. 1993.

MEDICAL APPLIANCE FOR IONIZING RADIATION TREATMENT HAVING RADIOPAQUE MARKERS

BACKGROUND OF THE INVENTION

This invention relates to the treatment of a portion of a body vessel by ionizing radiation, comprising radioactive radiation means arranged in a distal region of a core wire.

Endoluminal brachytherapy, and more particularly percutaneous transluminal brachytherapy currently face the problems inherent to the proper handling, energizing, transporting, sterilizing and accurate positioning of the equipment used for applying the therapy. And this is particularly an acute problem in the case of percutaneous transluminal brachytherapy where the lesion to be treated may be relatively difficult to reach and the risk of damaging areas increases substantially.

For example, U.S. Pat. No. 5,147,282 discloses a manual irradiation apparatus, more particularly suitable for intrabronchial and gynaecological irradiation treatment. The apparatus comprises a lead radiation shielding body with a longitudinally extending cable-receiving passage therein. A cable having radioactive seeds provided on one end thereof is received in the cable-receiving passage. During use, a catheter placed in the patient is joined to the shielding body and the portion of the cable bearing the radioactive source material is advanced through the cable-receiving passage in the shielding body and into the catheter. The document outlines that in preparation for an intrabronchial irradiation treatment, the patient's lesion was visually identified using a bronchoscope and, before retrieving the bronchoscope from the patient, the lesion boundary, i.e., beginning and ending locations of the lesion, were marked with two lead markers by taping them externally to the patient's chest. According to one embodiment, adapted for use with radiation sources other than a seeded cable, a shielding is constructed with a metallic tube running therein from end to end, extending through one end of the shielding body and extending through and beyond the other end thereof. This metallic tube is for allowing free passage of a plastic tandem closed at one end and containing radioactive tube sources maintained in the tandem by a plastic stopper insert. For loading the irradiation sources into the patient, an empty metal tandem is positioned in the patient and a docking tube with quick release connectors of the spring clip type with actuating levers at both ends is attached, one end to the shielding body and the other end to the patient's metal tandem. Then, using a loading-retrieval cable assembly, the plastic tandem containing the radioactive source and the stopper insert is pushed through the shielding body via the docking tube and into the metal tandem inserted into the patient. The shielding body and docking tube may then be removed and stored. When the irradiation treatment has been completed, the radioactive source must be removed by means of the loading-retrieval cable assembly. To this effect, the stopper insert is first removed from the plastic tandem and the docking tube and shielding body are connected again to the patient. To remove the radioactive source, the loading-retrieval cable assembly comprises a steel cable surrounded by a Teflon® tube, which steel cable is terminated by a solid tip extending out of the Teflon® tube and bears against a soft rubber ring located between the solid tip and the end of the Teflon® tube; the other end of the steel cable is attached to a retracting mechanism comprising a return spring urging the end of the steel cable and controlled by a set screw with concentric lock-up. With this frame, the loading-retrieval cable assembly may be advanced through the shielding body and docking tube and stopped at the opening of the plastic tandem containing the radioactive source and the cable solid tip and soft rubber ring, and passed inside the plastic tandem. The set screw of the retracting mechanism is triggered to retract the steel cable thereby forcing the solid tip to squeeze the soft rubber ring against the end of the Teflon® tube so that the soft rubber ring expands radially and grips the inner wall of the plastic tandem. The loading-retrieval cable assembly being thus connected to the plastic tandem containing the radioactive source, one may pull the cable out of the docking tube and retrieve the plastic tandem and radioactive source back to storage position inside the shielding apparatus. Reverse operation of the retracting mechanism disconnects the steel cable from the plastic tandem and the stopper insert may be re-inserted into the plastic tandem.

The document DE-9102312 shows use of a balloon catheter with a radioactive seed affixed to the end of a guide wire movable in a lumen of the balloon catheter. This document outlines the need to precisely locate the radioactive medium with respect to the lesion; it merely indicates, however, that the position of the radioactive medium can be precisely located at any time and that its position may be watched on a monitor, presumably a radioactive radiation detector, and by means of external markings, as referred to in the document.

In the case of usage of radioactive guide wires, there is a problem of safely securing the radioactive radiation source to the manipulating wire. The source can of course only be made of radiating material and will therefore always have only certain limited material properties. Another problem is that the source always has to be activated for itself, without the manipulation wire, because an activation together with the manipulation wire would also activate the wire, which would result in harmful radiation from the wire.

It is a primary object of the invention to provide a radioactive radiation equipment which is safe and devoid of hazardous or clumsy structures to assure accurate detection in the treatment area, and which permits a permanently watched treatment, even in narrow and/or tortuous vessels, remote locations and other difficult to reach areas. It is a further object of the invention to improve the conditions of locating, handling, energizing, transporting, assembling and sterilizing the materials used for endoluminal and more particularly percutaneous transluminal brachytherapy. It is still a further object of the invention to improve such conditions by means of an appliance that is versatile and simple to manufacture and easy to use.

SUMMARY OF THE INVENTION

Accordingly, as radiopaque means are used for positioning the radioactive radiation means on the distal region of the core wire, accurate and permanent monitoring by X-ray fluoroscopy is assured for the radioactive radiation means in addition to the securing of the conditions of their arrangement on the core wire. There is no risk of missing information between the position of the radiopaque visualization arrangement and the actual position of the radioactive radiation means, and such a result is secured whatever the configuration of the vessel and the location of the lesion. Because of the precise information on the radioactive radiation location, there is no risk of ineffective treatment and damage to regions which do not need the treatment. The appliance may be devised simply and without depending on the particular structural and material organization of the core wire. The radioactive radiation means may be transported, activated and handled separately of the core wire, and they may be easily assembled to the core wire, by means of the radiopaque means, under conventional radioactive protection environment, without any risk of having the radioactive radiation means erroneously or imprecisely placed with respect to the radiopaque visualizing structure. And sterilization may follow the assembly. Procedure of the treatment is greatly simplified in that the practitioner may readily follow a stenosis dilatation via a balloon expansion action by merely withdrawing the stiffening wire of the balloon and inserting on the place thereof the core wire equipped with the radioactive radiation means without the need of any other monitoring equipment than the X-ray fluoroscopy system used for positioning the balloon within the stenosis. And this is achieved with the highest precision and without any risk of improper placement of the radioactive radiation means. Advantageously, a balloon catheter closed at the distal end may be used to minimise contamination, with the possibility of precisely positioning the radioactive radiation means with the balloon, at the proper location where radioactive treatment is needed.

Where the radiopaque means comprise a first proximal radiopaque element and a second distal radiopaque element mounted on the core wire, with said first and second radiopaque elements maintaining the radioactive radiation means between them, an extremely accurate detection of the radioactive radiation means is achieved by providing a full locational information thereof along its length and from end to end. In parallel, the radioactive radiation means may be devised in simple cylindrical configurations, such as a tube, a coil, or a wire mesh surrounding the core wire, which structures are easy to be slidden on the core wire for installation thereon; and such cylindrical configurations of the radioactive radiation means have the added advantage of providing a radially uniform irradiation and dense concentration of the irradiation dose.

The first proximal and the second distal radiopaque elements may comprise coil configurations surrounding the core wire, which permits achieving a tolerance free assembly for the radioactive radiation means on the core wire because of the elasticity of the coil structures. In addition, these coil configurations allow a very fast assembly by sliding on the core wire, whereby the assembly may be easily, rapidly and safely made through driving channels for radiation protection purposes. And the coil configurations allow easy modulation of the stiffness of the assembly to meet the requirements of flexibility and pushability at that level of the core wire, while assuring a high density radiopaque configuration.

Where the first proximal radiopaque element is a coil having a proximal end affixed to the core wire, an easy and efficient assembly of the coil to the core wire may be achieved while providing the basic definition for the stacking assembly of the radioactive radiation means and second radiopaque element. When this proximal end of the first proximal radiopaque coil is soldered to the core wire, the assembly does not affect the configuration of the core wire and it may be easily made under radioactive radiation protection conditions. When the soldering tapers proximally, a smooth transition is assured between the coil and the core wire to avoid any obstacle creating protrusion which would disturb the movement of the core wire. And to achieve the most appropriate flexibility at the soldering level, the proximal end of the coil may have stretched turns.

Where the first proximal radiopaque element is a coil having a distal end affixed to the core wire, it is possible to further modulate the flexibility of the system at that level. When this distal end of the coil is soldered to the core wire, there is again the advantage of not affecting the configuration of the core wire while retaining the ease of action under radioactive radiation protection conditions. And where such a soldering tapers distally, a cone centering on the core wire is obtained for the proximal end of the radioactive radiation means with a substantially cylindrical configuration surrounding the core wire. To retain appropriate flexibility at that soldering level, the distal end of the coil may have stretched turns.

When the second distal radiopaque element comprises a coil at least partly squeezed on the core wire, the second distal radiopaque element may be rapidly and simply affixed to the core wire by a friction fit without any particular positional reference on the core wire, whereby variations in the length of the radioactive radiation means may be compensated without any difficulty of assembly. When such partly squeezed coil has a proximal and distal portions and an intermediate portion therebetween squeezed on the core wire, it becomes easy to have a coil configuration with proximal and distal ends that can assure a continuous transition with preceding and following surfaces which have to be circular. And when the intermediate portion deformably squeezes the core wire, a stronger fit is achieved between coil and core wire by the resulting interpenetration of turns of the coil into the surface of the core wire and the resulting deformation of both of them.

The partly squeezed coil may have a distal portion distally extending beyond the distal region of the core wire, whereby an unwanted stiffness is avoided at that level of the appliance where the core wire is already relatively stiff. This is of particular importance to advance the system through narrow curves and other difficult passages. This feature also results in a tolerance free assembly between the core wire and the coil while the coil still achieves its purpose of positioning the radioactive radiation means. The distal portion of the partly squeezed coil may terminate distally into a tip to be advanced through a catheter without the risk of standing against obstacles; and where the tip is a soldering with a substantially spherical surface, the tip can be made upon assembly of the system without the need of special tip parts.

The second distal radiopaque element (with the intermediate portion squeezed on the core wire) may further comprise a connection coil located proximally of the proximal portion of the partly squeezed coil, which connection coil is larger than the partly squeezed coil, and the proximal portion of the partly squeezed coil may be affixed to a distal portion of the connection coil. As the partly squeezed coil is flattened by the squeezing operation, its size increases perpendicularly to the squeeze; it is therefore advantageous to minimize that flat size increase by using a small diameter for the squeezed coil and to affix it to a larger connection coil in order to assure a smooth transition with the radioactive radiation means which have to be as thick as possible to have an appropriate mass for the radioactive energy.

When the proximal portion of the partly squeezed coil is meshing into the distal portion of the connection coil, a simple assembly is achieved without additional elements. And this proximal portion of the partly squeezed coil may have at least two stretched turns in order to achieve a pure friction lock between the two coils by raising the friction of the meshing turns; the assembly of the two coils is thus fully secured, without the need of glue which is not advisable in a radioactive environment or soldering which would increase the stiffness of the assembly.

And within the frame of the aforesaid two coil assembly for the second distal radiopaque element, the connection coil may have an outer diametrical size substantially in alignment with the cylindrical configuration of the radioactive radiation means, which assures the smoothest transition with the radioactive radiation means.

In sum, the present invention relates to a medical appliance for the treatment of a portion of a body vessel by ionizing radiation. The appliance has radioactive radiation means arranged in a distal region of a core wire and radiopaque means for positioning the radioactive radiation means on the distal region of the core wire. The radiopaque means may have a first proximal radiopaque element and a second distal radiopaque element mounted on the core wire, said first and second radiopaque elements maintaining the radioactive radiation means between them along the distal region of the core wire. The radioactive radiation means may comprise a substantially cylindrical configuration surrounding the core wire, such as a coil surrounding the core wire, a tube surrounding the core wire, or a wire mesh surrounding the core wire. The first proximal and second distal radiopaque elements may have coil configurations surrounding the core wire. The first proximal radiopaque element may be a coil having a proximal end affixed to the core wire, such as by soldering which may taper proximally. The proximal end of the coil may have stretched turns. The first proximal radiopaque element may be a coil having a distal end affixed to the core wire. The distal end of the coil may be soldered to the core wire, and the soldering may taper distally. The distal end of the coil may have stretched turns. The second distal radiopaque element may be a coil at least partly squeezed on the core wire, which may have proximal and distal portions and an intermediate portion therebetween squeezed on the core wire. The intermediate portion may deformably squeeze the core wire. The partly squeezed coil may have a distal portion distally extending beyond the distal region of the core wire. The distal portion of the partly squeezed coil may terminate distally into a tip, which may be a soldering with a substantially spherical surface. The second distal radiopaque element may also have a connection coil located proximally of the proximal portion of the partly squeezed coil, and the connection coil may be larger than the partly squeezed coil and the proximal portion of the partly squeezed coil may be affixed to a distal portion of the connection coil. The proximal portion of the partly squeezed coil may be meshed into the distal portion of the connection coil and may have at least two stretched turns. The connection coil may have an outer diametrical size substantially in alignment with the cylindrical configuration of the radioactive radiation means.

DESCRIPTION OF THE DRAWINGS

These and other objects, features and advantages of the invention will become readily apparent from the following detailed description with reference to the accompanying drawings which show, diagrammatically and by way of example only, a preferred but still illustrative embodiment of the invention.

DESCRIPTION OF THE PREFERRED EMBODIMENTS

Figure 1:
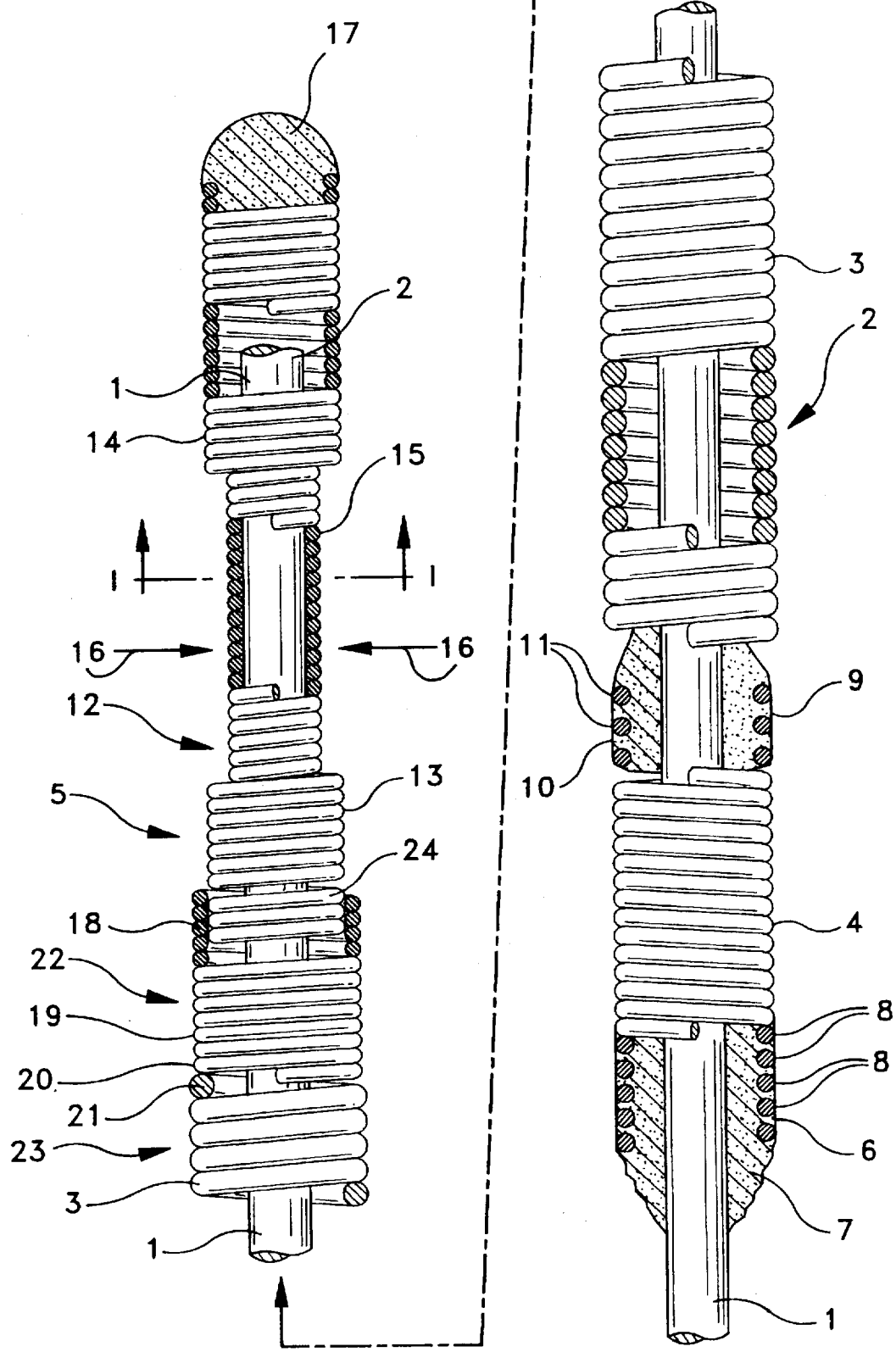
FIG. 1 is a longitudinal part sectional view of the appliance.
Figure 2:
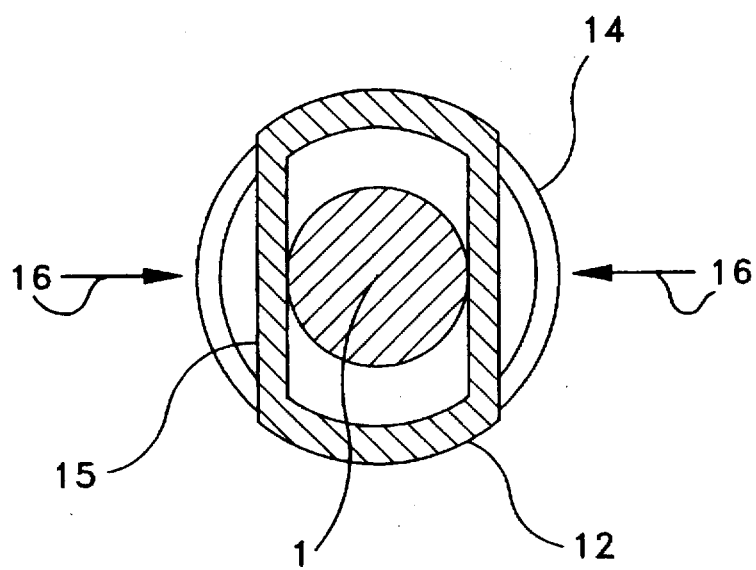
FIG. 2 is a sectional view according to line I—I of FIG. 1.

The medical appliance shown in FIGS. 1 and 2 comprises a core wire 1, preferably of stainless steel, for instance for use within the frame of a balloon catheter therapy, the core wire 1 has a proximal region (not shown) and a distal region 2 on which is mounted a coil 3 of radioactive material surrounding the core wire, such a radioactive material being for instance 90 Yttrium. Preferably, the coil 3 is made of a thick wire in order to have an important mass for energizing purposes.

The coil 3 is positioned on the core wire 1 by and between a first proximal coil element 4 and a second distal coil element 5 which therefore determine its location on the core wire and its fastening thereto. Coil elements 4 and 5 are made of a high density metal, preferably tungsten, in order to be highly radiopaque to provide vizualization via an X-ray fluoroscopy equipment.

Proximal coil element 4 surrounds the core wire 1 and has its proximal end 6 soldered at 7 to the core wire. This proximal end 6 has turns 8 which are stretched to get some more flexibility and the proximal end 6 is soldered to the core wire whereby the assembly remains somewhat flexible. The soldering 7 tapers proximally to make a smooth transition with the core wire 1. The distal end 9 of coil element 4 is also soldered at 10 on the core wire 1 and it has at that level some turns 11 which are stretched for more flexibility of the assembly. The soldering 10 tapers distally to provide a centering cone for the radioactive radiation coil 3.

The distal coil element 5 also surrounds the core wire 1 and comprises a coil 12 at least partly squeezed on the core wire 1. Coil 12 has a proximal portion 13 and a distal portion 14, and an intermediate portion 15 squeezed on the core wire 1, and therefore flattened as shown by arrows 16 and also shown on the section of FIG. 2. Preferably, the intermediate portion 15 deformably squeezes the core wire 1 in order to have an interpenetration between its turns and the surface of the core wire 1.

The coil 12 of coil element 5 has its distal portion 14 extending distally beyond the distal region 2 of the core wire 1 and terminating distally into a tip 17, preferably formed by a soldering with a substantially spherical surface.

The proximal portion 13 of coil 12 of coil element 5 has turns 18 meshing into a connection coil 19 which is larger than coil 12 and surrounds the core wire 1 proximally of coil 12 and which is a part of coil element 5 being made of the same highly radiopaque high density metal. The proximal end 20 of coil 19 is in contact with the distal end 21 of radioactive radiation coil 3 and its outer diametrical size 22 is substantially in alignment with the cylindrical configuration 23 of radioactive radiation coil 3. Two or more turns 24 among the turns 18 of the proximal portion 13 of coil 12 are stretched in order to provide a friction lock into coil 19.

Assembly of this appliance is obtained by first engaging and soldering the first proximal radiopaque coil 4 on the core wire 1, then engaging on the core wire the energized radioactive radiation coil 3, then engaging on the core wire the assembly 5 of connection coil 19 and connection coil 12 screwed therein with the tip 17 formed at the distal end thereof, and squeezing the intermediate portion 15 of coil 12 on the core wire 1 to assure fastening thereto.

After usage, the complete appliance may be disposed of under the legally required conditions once the energy of the radioactive radiation coil has reached the acceptable limit of radioactivity.

Variants are available without departing from the scope of the invention.

For instance, the coil 3 of radiation material may be replaced by other noncylindrical configurations or, preferably, other cylindrical configurations surrounding the core wire 1 such as a tube or a wire mesh.

In some realizations where the stepping due to the squeeze of the distal coil element 5 on the core wire is of less importance, it is possible to avoid use of the connection coil 19, the proximal end of coil 12 being then in contact with the distal end of radioactive radiation coil 3. It is also possible to avoid the connection coil 19 and to make the coil 12 as a two diameter coil.

The tip 17 may be made otherwise than by soldering, for instance by a fitted part.

Similarly, the solderings 7 and/or 10 for the first proximal coil element 4 may be replaced by tapered bushings friction fitting on the core wire or locked on the core wire, for instance by interpenetration of a rib of the bushing into a circular groove of the core wire.

And it would also be possible to replace one or the two radiopaque coil configurations for positioning the radioactive radiation means on the core wire by other structures as, for instance, radiopaque rings or bushings snap fitting on transverse grooves of the core wire.

And of course, only one of the radiopaque elements could be used for positioning the radioactive radiation element on the core wire, this sole element being affixed to the radioactive radiation element for locating and fastening purposes.

I claim:

1. A medical appliance for the treatment of a portion of a body vessel by ionizing radiation, comprising radioactive radiation means arranged in a distal region of a core wire and radiopaque means for positioning the radioactive radiation means on the distal region of the core wire, wherein the radiopaque means comprises a first proximal radiopaque element and a second distal radiopaque element mounted on the core wire, said first and second radiopaque elements maintaining the radioactive radiation means between them along the distal region of the core wire.

2. A medical appliance according to claim 1, wherein said radioactive radiation means comprises a substantially cylindrical configuration surrounding the core wire.

3. A medical appliance according to claim 2, wherein said radioactive radiation means comprises a coil surrounding the core wire.

4. A medical appliance according to claim 2, wherein said radioactive radiation means comprises a tube surrounding the core wire.

5. A medical appliance according to claim 2, wherein said radioactive radiation means comprises a wire mesh surrounding the core wire.

6. A medical appliance according to claim 2, wherein said first proximal and second distal radiopaque elements comprise coil configurations surrounding the core wire.

7. A medical appliance according to claim 6, wherein the first proximal radiopaque element is a coil having a proximal end affixed to the core wire.

8. A medical appliance according to claim 7, wherein said proximal end of the coil and the core wire are connected by solder.

9. A medical appliance according to claim 8, wherein the solder has a proximally tapered shape.

10. A medical appliance according to claim 8, wherein the proximal end of the coil has stretched turns.

11. A medical appliance according to claim 6, wherein the first proximal radiopaque element is a coil having a distal end affixed to the core wire.

12. A medical appliance according to claim 11, wherein said distal end of the coil and the core wire are connected by solder.

13. A medical appliance according to claim 12, wherein the solder has a distally tapered shape.

14. A medical appliance according to claim 12, wherein said distal end of the coil has stretched turns.

15. A medical appliance according to claim 6, wherein the second distal radiopaque element comprises a coil at least partly squeezed on the core wire.

16. A medical appliance according to claim 15, wherein said partly squeezed coil has proximal and distal portions and an intermediate portion therebetween squeezed on the core wire.

17. A medical appliance according to claim 16, wherein said the core wire is deformably squeezed by said intermediate portion.

18. A medical appliance according to claim 15, wherein said partly squeezed coil has a distal portion distally extending beyond the distal region of the core wire.

19. A medical appliance according to claim 18, wherein said distal portion of the partly squeezed coil terminates distally into a tip.

20. A medical appliance according to claim 19, wherein said tip comprises solder with a substantially spherical surface.

21. A medical appliance according to claim 16, wherein said second distal radiopaque element further comprises a connection coil located proximally of the proximal portion of the partly squeezed coil, and wherein said connection coil is larger than the partly squeezed coil and the proximal portion of the partly squeezed coil is affixed to a distal portion of said connection coil.

22. A medical appliance according to claim 21, wherein said proximal portion of the partly squeezed coil is meshed into the distal portion of the connection coil.

23. A medical appliance according to claim 22, wherein the proximal portion of the partly squeezed coil has at least two stretched turns.

24. A medical appliance according to claim 21, wherein said connection coil has an outer diametrical size substantially in alignment with the cylindrical configuration of the radioactive radiation means.

25. A medical appliance for the treatment of a portion of a body vessel by ionizing radiation, comprising radioactive radiation means arranged in a distal region of a core wire and radiopaque means for positioning the radioactive radiation means on the distal region of the core wire.

26. A medical device comprising:
   (a) a wire having a distal region;
   (b) a radiation source disposed about the wire distal region; and
   (c) a radiopaque marker disposed about the wire distal region a predetermined distance from the radiation source;
   wherein the medical device is sized and configured for percutaneous transluminal use.

27. A medical device comprising:
   (a) a wire having a distal region;
   (b) a radiation source disposed about the wire distal region;
   (c) a first radiopaque marker disposed about the wire distal region a first predetermined distance distally from the radiation source; and
   (d) a second radiopaque marker disposed about the wire distal region a second predetermined distance proximally from the radiation source; wherein the medical device is sized and configured for percutaneous transluminal use.

* * * * *